United States Patent [19]

Lin et al.

[11] Patent Number: 5,207,985
[45] Date of Patent: May 4, 1993

[54] KIT FOR USE IN ASSAY METHOD FOR THE DETERMINATION OF LITHIUM WITH NOVEL SUBSTITUTED CROWN DYES

[75] Inventors: Cheng-I Lin; Marcel Pirio, both of San Jose, Calif.

[73] Assignee: Syntex (U.S.A.) Inc., Palo Alto, Calif.

[21] Appl. No.: 718,067

[22] Filed: Jun. 20, 1991

Related U.S. Application Data

[62] Division of Ser. No. 164,025, Mar. 4, 1988, Pat. No. 5,049,666, which is a division of Ser. No. 866,821, May 23, 1986, Pat. No. 4,742,010.

[51] Int. Cl.$^5$ .............................................. G01N 33/20
[52] U.S. Cl. ...................................... 422/61; 436/73; 436/74; 436/79; 436/164; 534/652; 540/469; 568/644
[58] Field of Search ........................ 540/469; 534/652; 564/305; 568/644; 422/61; 436/73, 74, 79, 92, 164

[56] References Cited

U.S. PATENT DOCUMENTS

| | | | |
|---|---|---|---|
| 3,697,224 | 10/1972 | Means | 436/79 |
| 4,195,059 | 3/1980 | Whitcher et al. | 422/61 |
| 4,303,610 | 12/1981 | Sardisco et al. | 422/61 |
| 4,425,427 | 1/1984 | Luderer | 422/61 X |
| 4,504,368 | 3/1985 | Delton et al. | 540/469 X |
| 4,659,815 | 4/1987 | Pacey et al. | 436/79 X |

FOREIGN PATENT DOCUMENTS

| | | | |
|---|---|---|---|
| 0158445 | 1/1964 | U.S.S.R. | 436/79 |
| 1057500 | 11/1983 | U.S.S.R. | |

OTHER PUBLICATIONS

V. M. Ostrovskaya et al. Z. Obshch. Khim. (translation) 1977, 47, 157–162.
R. V. Sitnikova et al. Farmatsiya (Moscow) 1978, 27, 72–77.
V. M. Dziomko et al. Z. Obshch. Khim. (translation) 1981, 51, 2324–31.
R. V. Sitnikova Sud.-Med. Ekspert, 1979, 22, 41–43.
Dziomko et al. "Macrocyclic Formazans-Derivatives of [1, 11, 4, 5, 7, 8]-Dioxatetraazacyclotetradecine", Chem. Heterocyclic Comp. 1980, 15, 848–49 (translation of Khim. Geterotsikl. Soedin, 1979, 15, 1034–40).
Zolotov et al. "Macrocyclic Extractants" J. Anal. Chem. U.S.S.R., 1983, 37, 1187–1191 (translation of Zh. Anal. Khim., 1982, 37, 1543–48).
Sitrikov et al. "A Comparative Valuation of Li Determination by Spectrophotometric Methods in Biological Fluids" Lab. Delo. 1982, (3), 142–5.
Dziomko et al. Chemical Abstracts 1977, 86:171068h.
Dziomko V. M. "Nontraditional Nitrogen-Containing Macroheterocyclic Systems with a High Degree of Conjugation (Review)" Chem. Heterocyclic Comp. 1982, 18, 1–14 (translation of Khim. Geterosikl. Soedin. 1982, 8, 3–18).
Zalichenok et al. Chemical Abstracts 1977, 87:15487j.
Ostrovskaya et al. Chemical Abstracts 1977, 87:22606q.
Ostrovskaya et al. Chemical Abstracts 1977, 87:145267y.
Sitnikova et al. Chemical Abstracts 1979, 90:66316x.
Dziomko et al. Chemical Abstracts 1982, 96:52283w.
Sitrikova R. V. Chemical Abstracts 1982, 96:212391k.
Dziomko V. M. Chemical Abstracts 1986, 105:6419b.
Dziomko et al. Chemical Abstracts, 1980, 92:58836t.
Sitnikova Chemical Abstracts, 1980, 92:52886n.
Sitnikova et al. "Speckrophotometric Determination of Lithium with TMC-Crown Formazane" J. Anal. Chem. U.S.S.R., 1982, 37, 457–459 (translation of Zh. Anal. Khim., 1982, 37, 611–613).
Zelichenko et al. "Multidentate Formazans-Spectrophotometric Reagents for Lithium" J. Anal. Chem. U.S.S.R., 1976, 30, 1942–1945 (translation of Zh. Anal. Khim. 1975, 30, 2311–2315).

Primary Examiner—James C. Housel
Assistant Examiner—Arlen Sodarquist
Attorney, Agent, or Firm—Shalley G. Precivale; Theodore J. Leitereg; Carole F. Barrett

[57] ABSTRACT

Novel compounds and assay methods are provided for determining the presence of lithium in serum, plasma, urine or other sample without deproteinization. The novel compounds are water soluble derivatives of TMC-crownformazans and provide signal enhancement by increased absorbance of the dye-lithium complex over the dye anion.

8 Claims, No Drawings

KIT FOR USE IN ASSAY METHOD FOR THE DETERMINATION OF LITHIUM WITH NOVEL SUBSTITUTED CROWN DYES

This is a divisional of application Ser. No. 07/164,025, filed Mar. 4, 1988, now issued as U.S. Pat. No. 5,049,666, which in turn is a divisional of application Ser. No. 07/866,821, filed May 23, 1986, now issued as U.S. Pat. No. 4,742,010, the disclosures of which are incorporated herein by reference.

BACKGROUND OF THE INVENTION

1. Field of the Invention

This invention relates to new methods and compounds for determining lithium level in serum or other samples suspected of containing lithium, and more particularly to a homogeneous colorimetric method that is performed directly on the sample without deproteinization. Lithium in the form of lithium carbonate is administered to manic-depressive patients. The therapeutic range of lithium ion in plasma is quite narrow, namely, 0.8 to 1.2 mM. It is important to monitor the lithium level in such patients because of the toxic side effects that appear when the lithium level in blood exceeds the recommended level.

Current methods for detecting and determining lithium generally involve flame emission or atomic absorption methods. These techniques are disadvantageous because they are slow and labor intensive.

2. Description of the Related Art

Recently, colorimetric tests have been suggested for lithium analysis. R. V. Sitnikova et al in *Zh.Anal.-Khim.*, 37(4) 611–13(1982) disclose use of TMC-crownformazan (15, 16-dihydro-7-cyano-5H,17H-dibenzo [b,i] [1,11,4,5,7,8]-dioxa-tetraazacyclotetradecine) as a reagent to complex lithium. A spectometric method for determining lithium in plasma and urine was suggested using either the aforementioned crownformazan or a pyrazolone by R. V. Sitnikova et al in *Lab. Delo.* (3) 142–5(1980).

Use of TMC-crownformazan in lithium assays is disadvantageous. Such tests require the use of nearly water-free organic solvents, and therefore require that the sample be pretreated to remove protein which otherwise precipitates in the organic solvents and interferes with the assay. Further, only slight chromophoric changes are observed when crownformazan is used to complex lithium ion. Pyrazolones have been found to be both less selective and less sensitive than TMC-crownformazan. Further, tests using pyrazolones require deproteinization.

Use of an arsenophenyl ligand called Thoron in an alkaline acetone medium has been suggested by J. K. Trautman et al in *Talanta* 30(8) 587–91 (1983) for spectrophotometric determination of lithium. The dye solution suggested by Trautman et al is disadvantageous because it has a short shelf life, and sodium and other ions interfere with the results. Additionally, lithium assays using Thoron require deproteinization.

SUMMARY OF THE INVENTION

Methods and compositions are provided for the determination of the presence of lithium in a sample suspected of containing lithium. The method is a reliable and easily performed chromogenic assay for lithium in a sample suspected of containing lithium, including serum, plasma, urine, or the like without deproteinization. The method is carried out using the novel crownformazan chelating agents of the present invention. Signal enchancement is due to the enhanced absorbance of the dye-lithium complex over the dye anion. The compositions of the present invention are novel solubilized derivatives of TMC-crownforemazan.

In the method of the present invention the novel compounds are combined in an aqueous assay medium with a sample suspected of containing lithium, and the absorbance of the medium is measured.

Combinations of reagents are provided as kits to enhance the observed sensitivity of the assay by providing for ratios to substantially optimize the sensitivity for the range of interest of the lithium analyte. In addition to an aqueous solution of the TMC-crownformazan compounds of the present invention, the test kits can include a consolvent, for example, DMSO, or DMF.

DESCRIPTION OF THE SPECIFIC EMBODIMENTS

The present invention relates to a method for assaying for lithium. The method entails combining in an aqueous medium a test sample suspected of containing lithium ion with a novel crownformazan of the present invention as a complexing agent or chomogenic ionophore.

The aqueous medium is selected to avoid precipitation of components in the sample. It was found that the need for deproteinization of a sample in assays for lithium could be avoided by using novel water soluble derivatives of TMC-crownformazans in an aqueous assay medium. This medium can additionally contain polar cosolvents at concentrations below those that cause precipitation of serum proteins. The cosolvents increase the lithium affinity, and thus the sensitivity, of the assay. These cosolvents are usually polar organic substances of 1 to 12 atoms other than hydrogen, selected from carbon, oxygen, nitrogen, phosphorous, sulfur and halogen. Suitable cosolvents include dimethylsulfone, dimethylacetamide, tetrahydrofuran, dimethylsulfoxide (DMSO), sulfolane trimethylphosphate, dimethylformamide (DMF), dioxane, and the like. Within limits, the greater the amount of cosolvent used, the greater the sensitivity of the assay. The main limitation regarding the choice and concentration of the cosolvent is that sample components must not be precipitated. If the components are precipitated, a turbid solution results that will prevent accurate spectroscopic measurements. Therefore, cosolvent concentrations generally range from 0–75%, more usually 30–60%. Generally, cosolvent concentration depends on the nature of the sample, and the concentration of the lithium to be determined. All solutions are preferably filtered free of particulate matter to avoid light scattering.

Primarily, the method of the present invention is employed for determinations of lithium in blood and blood fractions such as serum and plasma; however, the method is usable for determinations of lithium in other body fluids such as urine, saliva, and the like. In general, the method of the present invention offers significant advantages over alternative methods when aqueous lithium solutions are to be analyzed. The present method offers particularly significant advantages when the aqueous lithium solution contains solutes that would precipitate in organic solvents.

The method of the present invention is usually conducted by combining a measured amount of an aqueous sample suspected of containing lithium or containing an unknown concentration of lithium with a reagent comprised of a novel crownformazan and an amine or ammonium hydroxide or an alkali metal hydroxide, other than lithium hydroxide. The aqueous solution is sufficiently alkaline so as to cause at least partial ionization of the crownformazan in the absence of lithium ion. Generally the ionization is about 5-100%. Preferably, ionization should be at least 80%. Potassium hydroxide in an aqueous solvent is preferred, but sodium hydroxide, or cesium or rubidium hydroxides and the like, are also usable. If the sample is believed to contain a high concentration of metal cation, for example sodium ion, it will usually be desirable to include sufficient concentration of that ion in the reagent so that the chromophoric response due to the ion is nearly saturated, and therefore will not change significantly as a result of introducing the ion from the sample into the assay mixture. If the sample is likely to contain a high concentration of sodium ion, for example, if a serum or urine is used, then an excess of sodium ion is added to the medium to minimize signal fluctuations due to serum sodium variations in the serum or urine sample. For this purpose, sodium ion generally is included in the reagent such that the sodium ion concentration is in excess of that expected after addition of the serum sample. If the sample is not believed to have a high sodium concentration, excess sodium ion is generally not added.

The method of the present invention is generally carried out at a pH in the range of 8 to 14, and preferably in the range of 10 to 14. Various bases may be used to achieve the desired pH during the determination. Illustrative bases include alkyl almines, Tris buffer, potassium phosphate, ammonia, guanidine and the like. The particular base employed is not critical to this invention, but in individual assays one base may be preferred over another.

Moderate temperatures are normally used for carrying out the method of the present invention, and usually constant temperatures during the period for conducting the method. The temperatures for the determination will generally range from about 0° to 50° C., more usually from about 15° to 40° C.

Considerations such as whether the assay is qualitative, semi-quantitative or quantitative will determine the concentration of the complexing agent. Generally, the concentration range of the lithium ion will determine the concentration of the complexing agent; however, the final concentration of the complexing agent is preferably determined empirically to optimize the sensitivity of the assay over the range of interest.

The lowest useful concentration of crownformazan is determined by the ability to detect the absorbance change and is thus dependent on various factors including the spectrometer sensitivity, path length of the light beam through the solution and the required range of the assay. The concentration of the crownformazan should be at least as great as the highest lithium concentration that is to be detected. In general, the lowest concentration of crownformazan will be about fivefold less than the dissociation constant of the lithium-crownformazan chelate under the assay conditions.

It will be understood that the highest useful concentration of crownformazan is also dependent in part on the spectrometric measurement capability of the instrument. Sufficient light must be transmitted to permit measurement of the difference between the absorbance with varying concentrations of lithium. In general, as the concentration of the crownformazan increases, the sensitivity of the assay will decrease because the ratio of modulated to unmodulated signal will decrease with increasing crownformazan concentration. Thus, the highest concentration of crownformazan will usually be no greater than 50 times, and preferably 20 times the lowest concentration of lithium that is to be detected.

The concentration of lithium in the sample to be assayed will generally vary from 0.1-1000 mM, usually about 0.1-2 mM, more usually from about 0.25 to 1.5 mM.

To determine the concentration of lithium, the assay response should be related to the response produced by a standard or calibrator containing a known concentration of lithium. Usually a standard curve will be constructed using two or more such calibrators. When a sufficiently high concentration of crownformazan is used, so that it never becomes more than about 40% bound by lithium even at the highest lithium concentration, the standard curve will approach linearity. Under these conditions, only one or two calibrators may be required.

A spectroscopic measurement is made at a wavelength that is defined for each novel crownformazan. Preferably, no separation or centrifugation steps are included in the assay. The measurement wavelength will usually be near the wavelength at which the absorbance of the crownformazan varies maximally as a function of lithium concentration. The wavelengths are generally in the range of about 480 to 600 nm, and more usually in the range of 480 to 520 nm.

Spectroscopic measurements may be direct or may be by difference. When by difference, an assay solution is placed in the reference compartment that is nearly identical to the assay solution containing the sample except that the assay solution in the reference will contain a known amount of lithium or no lithium.

The novel crownformazan chelating agents of the present invention form complexes with lithium. The agents are used without deproteinization of a sample to be analyzed in a colorimetric assay system that is capable of measuring pharmacologically significant levels of lithium with great accuracy and with substantially no interference from similar elements, such as sodium and potassium, and the like.

Preferably, solubilizing groups are attached para to the nitrogens on the aromatic rings ($R_4$) of the crownformazans of the present invention.

Substituents capable of rendering the composition soluble comprise a group of from 1 to 12 atoms other than hydrogen, selected from carbon, oxygen, nitrogen, phosphorous, sulfur and halogen. Solubilizing groups include carboxylic, phosphonic, sulfonic and phosphoric acids, amines, ethers, amides and alcohols other than phenols.

In such a case, the preferred solubilizing groups are those containing $COOH$, $CONH_2$, and $CONHCH_2COOH$. Independently selected solubilizing agents may also be attached meta to the nitrogens on the aromatic rings ($R_3$) of the crownformazan. In such a case, the preferred solubilizing group is one containing a sulfonic acid.

Additionally, the crownformazan of the present invention should contain an electron withdrawing group, such as, for example, $CN$, $NO_2$, $SO_2NX_2$, $CONX_2$ and $SO_2CF_3$ where X is independently selected from a group consisting of hydrogen and lower alkyl of about 1 to 2 carbon atoms, more preferably 1 carbon atom. $NO_2$ is the preferred electron withdrawing substituent.

The electron withdrawing group is attached to the carbon atom of the nitrogen containing bridge of the crownformazan.

The novel compounds of the present invention generally have the following structure:

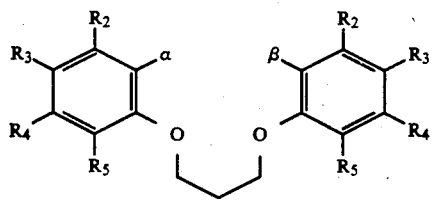

wherein:

α and β are NO₂ or NH₂ or can be taken together to form

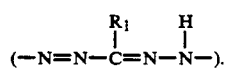

$R_1$ is an electron withdrawing group, such as, for example, —NO₂, —SO₂CF₃, —CONX₂, SO₂NX₂, or CN, wherein X is independently selected from a group consisting of hydrogen or lower alkyl containing about 1 to 2 carbon atoms, and more preferably 1 carbon atom.

$R_2$ and $R_5$ are independently selected from the group consisting of hydrogen, methoxy, carboxymethoxy, nitro, chlorine, fluorine and bromine, preferably hydrogen and fluorine.

$R_3$ and $R_4$ are independently selected from a group consisting of hydrogen and a hydrophilic substituent consisting of from 1 to 12 atoms other than hydrogen, which atoms are selected from the group consisting of carbon, oxygen, nitrogen, phosphorous, sulfur and halogen; with the proviso that no more than three of $R_3$ and $R_4$ are hydrogen.

Preferably at least one of $R_3$ and $R_4$ is selected from the group consisting of amines, amides, ethers, and carboxylic, phosphonic, sulfonic and phosphoric acids, esters thereof and alcohols other than phenol. $R_3$ is preferably hydrogen or —SO₃H. $R_4$ is preferably hydrogen, CO₂NH₂, —CO₂H, —SO₃H, or —CONHCH₂COOH.

A preferred embodiment has the aforementioned structure wherein α and β are both NH₂ and $R_3$ is —SO₃H. In an additional preferred embodiment α and β are both —NO₂ and $R_4$ is —CO₂H.

In another preferred embodiment the novel complexing agents of the present invention have the following structure:

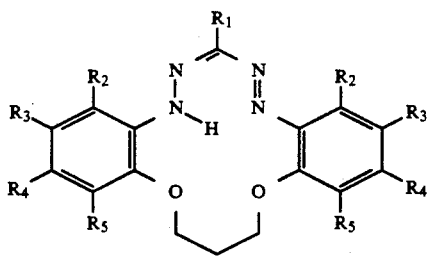

wherein:

$R_1$ is an electron withdrawing group, such as, for example, —NO₂, —SO₂CF₃, —CONX₂, SO₂NH₂, or CN, wherein X is independently selected from a group consisting of hydrogen or a lower alkyl containing about 1 to 2 carbon atoms, and more preferably 1 carbon atom.

$R_2$ and $R_5$ are independently selected from the group consisting of hydrogen, methoxy, carboxymethoxy, chlorine, bromine or fluorine, and preferably hydrogen and fluorine.

$R_3$ and $R_4$ are independently selected from a group consisting of hydrogen and a hydrophilic substituent consisting of from 1 to 12 atoms other than hydrogen. The atoms are selected from the group consisting of carbon, oxygen, nitrogen, phosphorous, sulfur and halogen; with the proviso that not more than three of $R_3$ and $R^4$ are hydrogen.

Preferably, at least one of $R_3$ and $R_4$ is selected from the group consisting of amines, amides, ethers, carboxylic, phosphonic, sulfonic and phosphoric acids, and alcohols other than phenol. $R_3$ is preferably hydrogen or —SO₃H. $R_4$ is preferably hydrogen, CO₂NH₂, —CO₂H, —SO₃H, or —CONHCH₂COOH.

In a further preferred embodiment the novel complexing agents have the following structure:

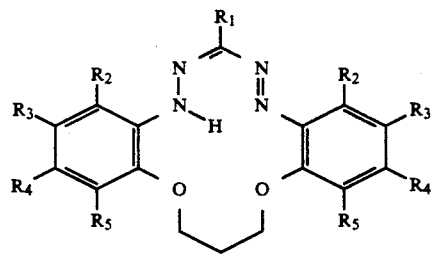

wherein: $R_1$ is NO₂; $R_2$, $R_3$ and $R_5$ are hydrogen; and $R_4$ is CO₂H.

In another preferred embodiment the novel complexing agents have the aforementioned structure wherein: $R_1$ is SO₂CF₃; $R_2$, $R_3$ and $R_5$ are hydrogen; and $R_4$ is CO₂H.

In an additional preferred embodiment the novel complexing agents have the aforementioned structure wherein: $R_1$ is NO₂; $R_2$, $R_3$ and $R_5$ are hydrogen; and $R_4$ is CONHCH₂CO₂H.

As a matter of convenience, the reagents for conducting an assay according to the present invention, can be provided in a kit in a packaged combination in predetermined amounts for use in assaying for lithium. The kit can comprise an aqueous alkaline solution, preferably potassium hydroxide, and a solution of the novel crownformazan composition of the present invention, for example, the nitro-bis carboxyl derivatives in an aqueous solvent solution. It is, also desirable for the kit to include an aqueous solution of about 40% to about 60% of a polar organic solvent, preferably dimethylsulfoxide. The kit may contain optional additional ingredients or ancillary agents as necessary such as, e.g., surfactants, and antimicrobial agents.

EXPERIMENTAL

All temperatures are in centigrade. All parts are by weight, except liquids which are by volume unless otherwise indicated. The following abbreviations are used: DMSO-dimethylsulfoxide; THF-tetrahydrofuran; NHSN-hydroxy succinimide; EtOAc-ethylacetate; TLC—thin layer chromatography.

EXAMPLE I 7-nitro-3,11-disulfo-16,17-dihydro-5H, 15H-dibenzo [b,i] [1,11,4,5,7,8] dioxatetraazacyclotetradecin(V)

A 500-ml round-bottom flask was equipped with a $CaCl_2$ drying tube and a magnetic stir bar and was charged with 11.1 g (0.090 mols) of nitrophenol, 8.24 g (0.040 mols) of 1,3-dibromopropane and 10 g (0.078 mols) of anhydrous $K_2CO_3$. The mixture was stirred magnetically and heated at 50° C. for 8 hours, and then an additional 4 g (0.032 mols) of nitrophenol were added and heating was continued overnight. The solvent was removed under vacuum with heating, and the residue was dissolved with EtOAc. The organic phase was extracted twice with 100 ml 10% $K_2CO_3$ solution. The organic extract was dried over $MgSO_4$ and concentrated in vacuo. The residue was crystallized from EtOAc/hexane, and the product (II) was found to have a melting point of 109°-110° C.

2 g (0.0063 mols) of the product (II) were dissolved in 20 ml of fuming sulfuric acid (20% $H_2SO_4.SO_3$) and the solution turned dark brown. After all the solid had dissolved and was stirred for an additional 5 minutes, the reaction was quenched with 50 ml of ice. The pH was adjusted to 5.0 with a saturated NaOH solution. After standing overnight at room temperature, a crystalline precipitate formed. The solid was filtered, and the cake was washed with ice cold water. The product (III) weighted 1.5 g after being dried over $P_2O_5$ in vacuo.

A 250-ml Parr hydrogenation vessel was charged with 500 mg (1.0 mmols) of the product (III), 50 ml (6/4) water/methanol, and 100 mg 10% palladium on carbon and, then was subjected to 50 psi hydrogen for 2.0 hr. The reaction mixture was filtered and the filtrate was concentrated in vacuo at 60° C. 400 mg of product IV was recovered.

300 mg (0.717 mmols) of product IV, 100 ml of water, and 2.0 ml concentrated HCl were mixed in a 500 ml flask and the solution was cooled in an ice bath to ~5° C., thereafter 0.148 g (0.002 mols) of $NaNO_2$ in 5 ml of water were added dropwise. After 3.5 hr, 0.131 g (0.002 mols) of nitromethane were added. The solution was stirred vigorously with dropwise addition of concentrated $NH_4OH$ and a dark cherry red solution formed. After the solution was stirred for one hour at pH 7.5-8.0, the solution was made acidic (pH 6.0) with 10% HCl and then concentrated to dryness at 40° C. in vacuo. Half of the material was subjected twice to chromatography on 5-20×20 cm 500 micron Analtech avicel F cellulose plates, eluant (1/1) methanol-water. The appropriate red band 1116I was extracted with water, concentrated in vacuo yielding 125 mg of product, dried under vacuum at 100° over $P_2O_5$ and found to have a melting point greater than 300° C.

EXAMPLE II 3,3'-(1,3-dioxopropyl)-4,4'-dinitrobismethyl Benzoate (VIII)

A 250-ml round-bottom flask equipped with a drying tube, condenser, and magnetic stir bar was charged with 10.7 g (0.058 mols) of 3-hydroxy-4-nitrobenzoic acid (VI) and 100 ml of thionyl chloride and refluxed overnight. The cooled reaction mixture was concentrated in vacuo with heating, and the residue was dissolved with 150 ml of ice-cold anhydrous methanol. After stirring at ambient temperature overnight, the solution was concentrated in vacuo and the product was crystallized from boiling hexane to give product VII having a melting point of 88°-89° C.

5 g (0.025 mols) of product VII were mixed with 6.9 g (0.05 mols) of anhydrous $K_2CO_3$ and 2.2 g (0.011 mols) of 1,3-dibromopropane in a 500-ml round-bottom flask equipped with a drying tube and magnetic stir bar. The reaction mixture was stirred at 50° C. for 16 hrs. An aliquot of the reaction mixture was spotted on TLC ($CH_2Cl_2$ silica gel plate).

The cooled reaction mixture was vacuum filtered and the solid was washed with DMF. The filtrate was added to 1.5 liters of ice-cold water and extracted several times with 500 ml $CH_2Cl_2$. The organic extracts were back washed with several times 200 ml 1N NaOH. The $CH_2Cl_2$ phase was dried with $MgSO_4$ and concentrated in vacuo. Product VIII was crystallized from acetone-ether and had a melting point of 148°-49° C.

EXAMPLE III 3,3'-(1,3-dioxopropyl)-4,4'-diaminobismethyl benzoate (IX)

1 g (0.0023 mols) of product VIII was dissolved in 250 ml ethyl acetate in a ml Parr hydrogenation flask with 200 mg 10% palladium on carbon and hydrogenated under 50 psi of $H_2$ for 15 minutes. The solution was filtered and filtrate concentrated in vacuo. The product IX was crystallized from ethyl-acetate-hexane and had a melting point of 151° to 152° C.

EXAMPLE IV 7-carbonitrile-2,12-dimethoxycarbonyl, 16,17-dihydro-5H, 15H-dibenzo [b,i] [1,11,4,5,7,8] dioxatetraacyclotetradecin (X)

A mixture of 750 mg (2 mmols) of the product of Example III and 4.5 ml 1N hydrochloric acid in 200 ml of water was cooled to 2° C. 276 mg (4 mmols) of sodium nitrite in 10 ml of water were added dropwise to the solution and after 3 hours the diazonium solution was added dropwise to a stirring solution of 212 mg (2.5 mmols) of cyanoacetic acid and 1.5 ml 6N NaOH in 100 ml water. The solution was stirred overnight at ambient temperature and acidified with concentrated HCl. A dark red precipitate was formed and the solid material was collected and then dissolved in $CH_2Cl_2$, dried with $MgSO_4$ and concentrated in vacuo. Chromatography purification on Analtech silica gel GF 1000 micron plates, eluant ethyl acetate hexane. The product (X) was crystallized from chloroform yielded dark brown crystals with a melting point of more than 300° C.

EXAMPLE V 7-trifluoromethylsulfonyl-2,12-dimethoxycarbonyl-16,17-dihydro-5H,15H-dibenzo [b,i] [1,11,4,5,7,8] dioxatetraacyclotetradecin (XI)

250 mg (0.668 mmols) of the product of Example III were dissolved in 50 ml of THF and cooled to 4° C. with an ice bath. 156 mg (1.3 mmols) of isoamyl nitrite and 130 mg (1.3 mols) of sulfuric acid were added, and then 1.5 ml of water was added to dissolve the precipitate which formed. After 2 hours, the reaction mixture was added dropwise to a stirring solution of 100 mg (1.2 mmols) trifluorodimethyl sulfone, 2 ml 1N NaOH, 25 ml of 10% sodium acetate, and 25 ml water. After 1.5 hr, the reaction was extracted with two 50 ml portions of ethyl ether. The organic phase was dried with $MgSO_4$ and concentrated in vacuo. The residue was chromatographed on 3-20×20 cm 1000 micron Analtech silica gel GF plates, eluant (2/8) hexane-ehtyl acetate. The appropriate bands were extracted with ethyl acetate and concentrated, yielding 210 mg of product XI.

EXAMPLE VI 7-carbonitrile-2,12-dimethoxycarbonyl-4,10-dinitro-16,17-dihydro-5H,15H dibenzo [b,i] [1,11,4,5,7,8] dioxatetraacyclotetradecin (XIII)

A 150-ml round-bottom flask equipped with a magnetic stir bar was charged with 1.0 g (0.0028 mols) of product IX and 30 ml of glacial acetic acid. To this stirring solution was added dropwise an ice-cooled solution of 0.152 ml concentrated $H_2SO_4$ in 100 ml of glacial acetic acid and the solution had a slight pink color and a precipitate was formed. 6 ml of 90% fuming nitric acid were added dropwise to an ice cold 20 ml solution of glacial acetic acid and the resulting solution was added dropwise to the above diamine solution. The reaction mixture was stirred with heating at 55° C. for 32 hours.

The reaction was poured into 200 ml $CH_2Cl_2$ and extracted several times with 200 ml ice water. The organic phase was extracted with four 200 ml portions of 0.1N NaOH, dried over $MgSO_4$ and concentrated in vacuo. Chromatography on 10-20×20 cm 1000 micron Analtech silica gel GF plates, eluant (1/9) MeOH/$CH_2Cl_2$. The appropriate bands were extracted and subjected again to the above chromatography conditions. 0.97 g of 3,3'-(1,3-dioxopropyl)-4,4'-diamino-5,5'-dinitro bismethyl benzoate (XII) were recovered, and had a melting point of 208°–210° C.

100 g (0.215 mmols) of XII were dissolved in 25 ml THF and cooled to 4° C. in ice bath with stirring and then 51 mg (0.430 mmols) of isoamyl nitrite and 57.2 μl $H_2SO_4$ were added and stirred for 3 hours. The resulting solution was added dropwise to 40 (0.470 mmols) of cyanoacetic acid which had been dissolved in 5 ml 1N NaOH and 100 ml $H_2O$ at 4° C. After 30 minutes, 80 mg of cyanoacetic acid were added and allowed to stir for 3 hours at room temperature. The crude reaction mixture was extracted with three 100 ml portions of $CH_2Cl_2$, dried $MgSO_4$, filtered and concentrated.

Purification by preparative TLC on four 20×20 cm, 1000 micron Analtech silica gel GF, eluant ethyl acetate. The appropriate band was extracted with methanol dichloromethane. The dry product was taken up in dichloromethane and filtered through a fine glass funnel and 20 mg of compound XIII were recovered.

EXAMPLE VII

Saponification of 3,3'-(1,3-dioxopropyl) 4,4'-dinitrobismethyl benzoate (VIII)

8 g (0.022 mols) of product VIII was dissolved in 30 ml 1N NaOH, 150 ml THF, and 40 ml MeOH. The solution was stirred at ambient temperature for about 16 hr. To the clear reaction mixture 350 ml of water were added, followed by dropwise addition of concentrated HCl. The white precipitate was filtered and washed with 500 ml water. The resulting white solid was dried over $P_2O_5$ under vacuum to yield 9.3 g of 3,3'-(1,3-dioxopropyl-4,4'-bisbenzoic acid (XIV) with a melting point greater than 300° C.

EXAMPLE VIII 3,3'-(1,3-dioxopropyl)-4,4'-diaminobisbenzoic acid (XV)

A mixture of 3 grams of the product of Example VII (3 g) 200 ml water, and sufficient concentrated $NH_4OH$ to cause dissolution was hydrogenated under 50 psi hydrogen pressure for 3 hours.

The solution was filtered and concentrated in vacuo. The resulting light brown solid was dried over $P_2O_5$ under vacuum to yield 2.5 g of the product (XV), with melting point 234°–235° C.

EXAMPLE IX 7-trifluoromethylsulfonyl-2,12-dicarboxyl-16,17-dihydro-5H,15H,dibenzo [b,i] [1,11,4,5,7,8] dioxatetraazacyclotetradecin (XVI)

500 mg (1.44 mmols) of the product of Example VIII were dissolved in 0.25M HCl with heating, and 6 ml of THF were added, and the solution was stirred and cooled in an ice bath to ~5° C. 200 mg (2.88 mols) sodium nitrite dissolved in 10 ml $H_2O$ were added dropwise to the solution and it turned light green yellow. After 1 hour, the diazonium solution was added dropwise to a vigorously stirring solution of 40 ml 0.25N NaOH, 20 ml THF, and 850 mg (5.76 mmols) of trifluorodimethyl sulfone. The pH was increased during the reaction to 9.5–10 with 1N NaOH. After 30 minutes, the product was acidified with concentrated HCl, extracted twice with 200 ml ethyl ether, dried with $MgSO_4$, filtered and concentrated. Purification of 50 mg of crude product by column chromatography using 5×16 cm column of Merck silanised silica gel 60 PF-254, eluant ethyl ether. Fractions were pooled, filtered through a fine-glass funnel, and concentrated. The residue was dissolved in 10 ml water with $NH_4OH$, precipitated with HCl and centrifuged. The pellet was resuspended in water and centrifuged. The pellet was then dried at 100° C. over $P_2O_5$ under vacuum and 25.6 mg of XVI having molecular weight 517.4 were recovered.

EXAMPLE X 7-nitro-2,12-dicarboxyl-16,17-dihydro-5H,15H-dibenzo [b,i] [1,11,4,5,7,8] dioxatetraacyclotetradecin (XVII)

800 mg of the product of Example VIII, 150 ml of water, and 4 ml of concentrated hydrochloric acid were mixed and then cooled to 5° C., whereupon 637 mg (9.2 mmols) of sodium nitrite were added. After stirring for 2.5 hours in an ice bath, 554 mg (9.2 mmols) of nitromethane were added at once to the solution, and concentrated $NH_4OH$ was added and the resulting solution had pH 8.0. After 2.5 hours, the solution was made acidic (pH 6.0) with concentrated HCl, and the precipitate was centrifuged and the solid washed twice with 200 ml of water, centrifuged and dried at 100° C. over $P_2O_5$ in vacuo. The product contained impurities that remain at base line using TLC silica gel GF, (0.5/95) $NH_4OH$—MeOH system. To purify the product, an aliquot of the material was suspended in a minimum amount of methanol and concentrated $NH_4OH$ was added to cause dissolution, then applied atop a dry packed column 4×15 cm of E. Merck silica gel 60 and eluted with 1% $NH_4OH$—MeOH. After monitoring by TLC silica gel GF, eluant 5 drops $NH_4OH$/10 ml MeOH, the appropriate fractions were pooled and concentrated in vacuo. The residue was taken up in water NH4OH and acidified with HCl and centrifuged. This was repeated twice on the pellet and then washed with methanol. The pellet was dried at 100° C. over P2O5 in vacuo, yielding 150 mg of compound XVII having a molecular weight of 430.4.

EXAMPLE XI 7-nitro-2,12,di(N-carbonyl glycine)-16,17-dihydro-5H, 15H-dibenzo [b,i] [1,11,4,5,7,8] dioxatetraacyclotetradecin (XXI)

2.5 g (0.0073 mols) of the product of Example VII, 1.5 g (0.0073 mols) of N,N'-dicyclohexylcarbodiimide, 0.839 g (0.0073 mols) of NHS, and 50 ml of anhydrous DMF were mixed and stirred at ambient temperature for 16 hours. 4.6 g (0.0366 mols) of glycine methyl ester hydrochloride were dissolved in 40 ml DMF and 3.7 g (0.0366 mols) of triethylamine were added, and after ½ hour, this solution was filtered rapidly into the above activated NHS solution and left stirring overnight. The reaction mixture was concentrated under high vacuum to a residue, and was taken up in 100 ml dichloromethane and filtered. The filtrate was extracted twice with 100 ml of 0.1N HCl dried MgSO4, filtered and concentrated.

Half of the residue was chromatographed using TLC on 20-20×20 cm 1000 micron Analtech silica GF plates and eluted with 5% MeOH-95% CH2Cl2. The appropriate bands were pooled, extracted with MeOH—CH2Cl2 and concentrated and yielded 1.6 g of product XVIII with molecular weight 548.

1.5 grams of compound XVIII, 25 ml 1N NaOH, 100 ml THF, and 20 ml methanol were mixed and stirred for 16 hr at room temperature. TLC analysis Analtech silica gel GF (1/0.9) MeOH—CH2Cl2 showed no starting material remaining.

100 ml of water were added and the organic solvents removed on a rotary evaporator. The solution was made acidic with concentrated HCl (pH 3.0). A white precipitate (compound XIX) was collected and was dried over P2O5 in vacuo, and yielded 1.2 g. Compound XIX has a molecular weight of 520.4.

A mixture of 1.2 g (0.002 mols) of Compound XIX, 100 ml absolute methanol, and ~0.4 ml of concentrated NH4OH and 100 mg 10% palladium on carbon was hydrogenated under 50 psi hydrogen pressure for 2.5 hours. The catalyst was removed by filtration, and the filtrate was concentrated in vacuo, yielding 0.88 g of a light violet product (compound XX) having a molecular weight of 460.4.

400 mg (0.87 mmols) of compound XX, 150 ml of water, and 5 ml concentrated HCl were mixed and the solution was cooled to ~5° C., and 120 mg (1.74 mmols) of sodium nitrite in 10 ml of water were added dropwise. A light yellow clear solution was formed. After 3.5 hours, 106 mg (1.74 mmols) of nitromethane were added and the solution stirred vigorously with the dropwise addition of concentrated NH4OH. A deep red solution formed, and the pH was maintained below 8.5. After stirring for 1.5 hours, the reaction was brought to pH 5.0 with hydrochloric acid. The precipitate was centrifuged, and the pellet was resuspended in water and centrifuged. This procedure was repeated using methanol. The pellet was dried in vacuo over P2O5 at 100° C. The crude product was dissolved in MeOH-NH4OH, absorbed on Baker silica gel 60, and applied atop a 2.5×12 cm silica gel 60 column, eluted with 4% NH4OH-96% MeOH and appropriate fractions pooled, concentrated in vacuo. The residue was dissolved in NH4OH—H2O and precipitated with HCl and centrifuged. The pellet was suspended in water and centrifuged. The pellet was dried over P2O5 at 100° C. in vacuo. 210 mg of compound XXI were recovered.

EXAMPLE XII

In order to demonstrate the efficacy of compounds of the present invention, the compounds were employed in a number of assays for lithium. In carrying out the assay a Gilford Stasar III spectrophotometer was employed, but any spectrophotometer can be used. A pipettor-dilutor and a CP5000 printer were also employed. The following solutions are prepared as reagents for use in the assay.

Buffer

55% DMSO/45% H2O containing 0.055N KOH and 6.85 mM NaCl

Complexing Agent $9.3 \times 10^{-4}$M compound XVII in 55% DMSO/45% H2O

Calibrators

1. Low: $1.25 \times 10^{-4}$M Li2CO3 and 154 mM of NaCl in H2O corresponding to lithium ion concentration of 0.25 μmole/ml
2. High: $7.5 \times 10^{-4}$M Li2CO3 and 154 mM of NaCl in H2O corresponding to lithium ion concentration of 1.5 μmole/ml The protocol employed for carrying out an assay is as follows: 1) 60 microliters of the sample was drawn up and dispensed with 300 microliters of buffer into a Croan cup. 2) 60 μl of diluted serum was transferred into a Croan cup and 300 μl Buffer was then added. 3) 60 microliters of the complexing agent were added to the diluted serum, followed by the addition of 300 μl of Buffer. The entire sample was mixed and aspirated into the spectrophotomer. After 18 seconds a reading was taken. Emission was measured at 550 nm.

A blank was carried out by repeating the above procedure using Buffer in place of the Complexing Agent. Two to three readings were recorded for both sample and blank. These values were averaged and then substracted to yield the final value for comparison with a standard curve.

The results are summarized below.

TABLE 1

| Lithium ion (μmole/ml) | Absorption (units) |
| --- | --- |
| 0.25 | 2376 |
| 1.5 | 2570 |

For purposes of comparison, the correlation between the assay of the present invention and atomic absorption assay was as follows:
Slope: 1.054
Intercept: −0.028
Corr.: 0.994
S.E.E.: 0.03
N: 28
wherein S.E.E. is standard estimated error and N is the number of patient samples.

The subject assay provides for a sensitive accurate method of determining lithium in serum and the like. The subject invention provides novel complexing agents for lithium which when employed in the method of the present invention provide a method for qualitatively and quantitatively determining lithium without deproteinization of the sample of interest, such as serum. The method is rapid and the protocol is simple and relatively free of technician introduced error. A two point standard curve can be used for the assay. The assay can be carried out without the use of enzyme and antibody reagents.

Although the foregoing invention has been described in some detail by way of illustration and example for purposes of clarity and understanding, it will be obvious that certain changes and modifications may be practiced within the scope of the appended claims.

What is claimed is:

1. A kit for use in an assay for lithium, said kit comprising in a packaged combination:
   (a) a compound having the formula:

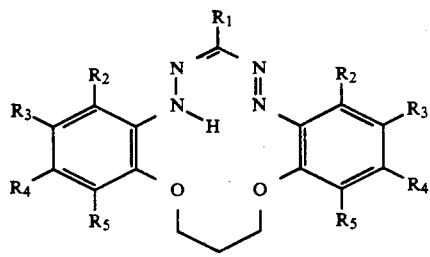

wherein:
   $R_1$ is an electron withdrawing group, selected from the group consisting of $-NO_2$, $-SO_2CF_3$, $-CONX_2$, and $-SO_2NX_2$, and X is independently selected from the group consisting of hydrogen, methyl and ethyl;
   $R_2$ and $R_5$ are independently selected from the group consisting of hydrogen, methoxy, carboxymethoxy, nitro, chlorine, bromine and fluorine; and
   $R_3$ and $R_4$ are independently selected from the group consisting of hydrogen and a hydrophilic substituent consisting of from one to twelve atoms other than hydrogen, which atoms are selected from the group consisting of carbon, oxygen, nitrogen, phosphorous, sulfur and halogen; with the proviso that not more than three of $R_3$ and $R_4$ are hydrogen; and
   (b) an aqueous buffer solution of pH of about 8 to about 14.

2. A kit for use in an assay according to claim 1 which further comprises a polar solvent selected from the group consisting of dimethylsulfoxide, dimethylformamide, tetrahydrofuran, dimethylsulfone, dimethylacetamide, and mixtures thereof.

3. A kit for use in an assay for lithium, said kit comprising in a packaged combination:
   (a) a compound having the formula:

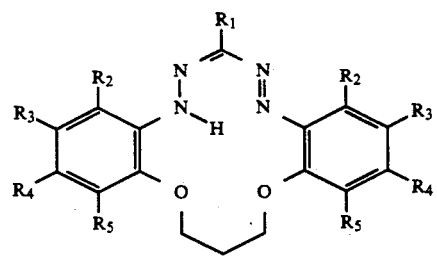

wherein:
   $R_1$ is $NO_2$;
   $R_2$, $R_3$ and $R_5$ are H; and
   $R_4$ is $CO_2H$; and
   (b) an aqueous buffer solution of pH of about 8 to about 14.

4. A kit for use in an assay according to claim 3 which further comprises a polar solvent selected from the group consisting of dimethylsulfoxide, dimethylformamide, tetrahydrofuran, dimethylsulfone, dimethylacetamide, and mixtures thereof.

5. A kit for use in an assay for lithium, said kit comprising in a packaged combination:
   (a) a compound having the formula:

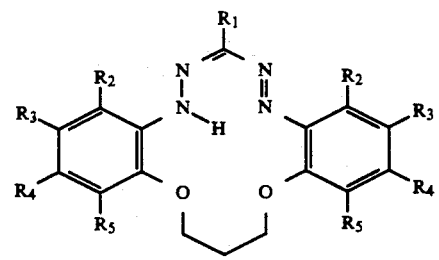

wherein:
   $R_1$ is $SO_2CF_3$;
   $R_2$, $R_3$ and $R_5$ are H; and
   $R_4$ is $CO_2H$; and
   (b) an aqueous buffer solution of pH of about 8 to about 14.

6. A kit for use in an assay according to claim 5 which further comprises a polar solvent selected from the group consisting of dimethylsulfoxide, dimethylformamide, tetrahydrofuran, dimethylsulfone, dimethylacetamide, and mixtures thereof.

7. A kit for use in an assay for lithium, said kit comprising in a packaged combination:
   (a) a compound having the formula:

wherein:
   $R_1$ is $NO_2$;
   $R_2$, $R_3$ and $R_5$ are H; and
   $R_4$ is $CONHCH_2CO_2H$; and
   (b) an aqueous buffer solution of pH of about 8 to about 14.

8. A kit for use in an assay according to claim 7 which further comprises a polar solvent selected from the group consisting of dimethylsulfoxide, dimethylformamide, tetrahydrofuran, dimethylsulfone, dimethylacetamide, and mixtures thereof.

* * * * *